United States Patent
De Lange et al.

(10) Patent No.: US 9,630,906 B2
(45) Date of Patent: Apr. 25, 2017

(54) AMINE SALTS OF PITAVASTATIN AND ROSUVASTATIN

(71) Applicant: DSM SINOCHEM PHARMACEUTICALS NETHERLANDS B.V., Delft (NL)

(72) Inventors: Ben De Lange, Echt (NL); Henricus Leonardus Marie Elsenberg, Echt (NL); Karin Henderika Maria Bessembinder, Echt (NL)

(73) Assignee: DSM Sinochem Pharmaceuticals Netherlands B.V., Delft (NL)

( * ) Notice: Subject to any disclaimer, the term of this patent is extended or adjusted under 35 U.S.C. 154(b) by 0 days.

(21) Appl. No.: 14/780,845

(22) PCT Filed: Mar. 28, 2014

(86) PCT No.: PCT/EP2014/056267
§ 371 (c)(1),
(2) Date: Sep. 28, 2015

(87) PCT Pub. No.: WO2014/154856
PCT Pub. Date: Oct. 2, 2014

(65) Prior Publication Data
US 2016/0052864 A1 Feb. 25, 2016

(30) Foreign Application Priority Data

Mar. 29, 2013 (EP) ..................................... 13161843
Aug. 29, 2013 (EP) ..................................... 13182231

(51) Int. Cl.
*C07C 209/78* (2006.01)
*C07C 211/63* (2006.01)
*C07D 215/14* (2006.01)
*C07D 239/42* (2006.01)
*C07D 307/52* (2006.01)

(52) U.S. Cl.
CPC .......... *C07C 209/78* (2013.01); *C07C 211/63* (2013.01); *C07D 215/14* (2013.01); *C07D 239/42* (2013.01); *C07D 307/52* (2013.01)

(58) Field of Classification Search
CPC ... C07C 209/78; C07C 211/63; C07D 215/14; C07D 239/42; C07D 307/52
See application file for complete search history.

(56) References Cited

FOREIGN PATENT DOCUMENTS

| CA | 2 813 388 | 4/2012 |
|----|-----------|--------|
| EP | 0 520 406 | 12/1992 |
| EP | 2 383 260 | 11/2011 |
| WO | WO 2006/136407 | 12/2006 |
| WO | WO 2008/038132 | 4/2008 |
| WO | WO 2010/027060 | 3/2010 |
| WO | WO 2010/035284 | 4/2010 |
| WO | WO 2012/063115 | 5/2012 |
| WO | WO 2012/106584 | 8/2012 |
| WO | WO 2012/176218 | 12/2012 |
| WO | WP 2013/037838 | 3/2013 |

OTHER PUBLICATIONS

International Search Report for PCT/EP2014/056267, mailed Jul. 1, 2014, 8 pages.
Nadkarni et al., "Preparation of 1-(diphenylmethyl) piperazine salt of rosuvastatin", Chemical Abstracts Service, XP002699997, Jul. 27, 2012, 2 pages.
Bhemireddy et al., "Rosuvastatin amine and indanamine salts and process for preparation thereof", Chemical Abstracts Service, XP002699998, Jul. 13, 2012, 7 pages.
Mahajan et al., "A process for the preparation of pitavastatin calcium for use as a HMG-CoA reductase inhibitor", Chemical Abstracts Service, XP002699999, Oct. 19, 2012, 2 pages.
Nadkarni et al., "Preparation of L-valine benzyl ester salt of rosuvastatin", Chemical Abstracts Service, XP002700000, Jul. 27, 2012, 2 pages.
Reddy et al., "Preparation of novel amine salts of statin drugs", Chemical Abstracts Service, XP002700001, Sep. 11, 2009, 2 pages.

*Primary Examiner* — Erich A Leeser
(74) *Attorney, Agent, or Firm* — McNeely, Hare & War, LLP; William D. Hare

(57) ABSTRACT

The present invention relates to unsaturated amine salts of HMG-CoA reductase inhibitors, to a method of producing said amine salts and to the use of said amine salts in the production of pharmaceutically acceptable salts of HMG-CoA reductase inhibitors.

2 Claims, No Drawings

AMINE SALTS OF PITAVASTATIN AND ROSUVASTATIN

This application is the U.S. national phase of International Application No. PCT/EP2014/056267 filed 28 Mar. 2014, which designated the U.S. and claims priority to EP Patent Application Nos. 13161843.1 filed 29 Mar. 2013, and 13182231.4 filed 29 Aug. 2013, the entire contents of each of which are hereby incorporated by reference.

FIELD OF THE INVENTION

The present invention relates to unsaturated amine salts of HMG-CoA reductase inhibitors, to a method of producing said amine salts and to the use of said amine salts in the production of pharmaceutically acceptable salts of HMG-CoA reductase inhibitors.

BACKGROUND OF THE INVENTION

HMG-CoA reductase inhibitors, also known as statins, are widely used drugs prescribed to treat hypercholesterolemia, hyperlipoproteinemia, and atherosclerosis. Examples of HMG-CoA reductase inhibitors are atorvastatin, fluvastatin, lovastatin, mevastatin, pitavastatin, pravastatin, rosuvastatin and simvastatin.

Production of HMG-CoA reductase inhibitors is known and includes (bio)-chemical conversion, chromatography, crystallization extraction, fermentation and the like. Some HMG-CoA reductase inhibitors, like lovastatin, are produced by fermentation using microorganisms of different species identified as species belonging to *Aspergillus, Monascus, Nocardia, Amycolatopsis, Mucor* or *Penicillium* genus. Some, like mevastatin, pravastatin and simvastatin, are obtained by treating the fermentation products using the methods of chemical or enzymatic synthesis. Others, like atorvastatin, fluvastatin, pitavastatin and rosuvastatin, are the products of total chemical synthesis.

In several cases, production of HMG-CoA reductase inhibitors includes isolation and purification through salt formation. For example, in U.S. Pat. Nos. 4,319,039 and 4,342,767, the ammonium salt of lovastatin is isolated from the organic phase which has been extracted from the fermentation medium. In the same documents the ethylene diamine, tetramethyl ammonium, potassium and N-methyl-glucamine salts as well as salts of different amino acids such as L-arginine, L-lysine and L-ornithine is described. EP 65,835 discloses the preparation of the tert-octyl amine and L-ornithine salts of certain modified HMG-CoA reductase inhibitors, whereby also other salts with amines such as ammonia, amino acids or organic amines like benzyl amine, cycloheptyl amine, cyclohexyl amine, cyclopentyl amine, dibenzyl amine, dicyclohexyl amine, N,N-diethylbenzyl amine, N,N-diethylcycloheptyl amine, N,N-dimethylbenzyl amine, N,N-dimethylcyclohexyl amine, N,N-dimethylcyclopentyl amine, N-ethylcycloheptyl amine, N-ethylcyclohexyl amine, 2-ethylhexyl amine, N-ethyl-N-methylbenzyl amine, N-methylbenzyl amine, 2-methylbenzyl amine, N-methylcyclopentyl amine, N-methylpiperidine, N-methylpyrrolidine, morpholine, octyl amine, phenethyl amine, piperidine, pyrrolidine and tribenzyl amine are mentioned. U.S. Pat. Nos. 5,763,646 and 5,763,653 disclose the preparation of the cyclopropyl amine and n-butyl amine salts of lovastatin and their use in a process of chemical semi synthesis of simvastatin. U.S. Pat. No. 5,403,860 discloses amine salts of octahydronaphthalene oxime derivatives of HMG-CoA reductase inhibitors ML-236A, ML-236B, MB-530A and MB-530B. As final amine salts, dibenzyl amine, dicyclohexyl amine, D-glucosamine, morpholine, tert-octyl amine and D-phenylglycine alkyl ester salts are mentioned. WO 00/17150 describes amine salts of HMG-CoA reductase inhibitors in the process for semi synthetic preparation of HMG-CoA reductase inhibitors and the conversion of the amine salts of HMG-CoA reductase inhibitors into the pharmaceutically acceptable salts of the HMG-CoA reductase inhibitors. WO 00/17150 mentions atorvastatin, fluvastatin, lovastatin, mevastatin, pravastatin and simvastatin as HMG-CoA reductase inhibitors on the one hand and a wide range of alkyl amines on the other hand, preferred examples of which are straight, branched or cyclic alkyl amines such as tert-amyl amine, n-butyl amine, sec-butyl amine, tert-butyl amine, cyclohexyl amine, dibutyl amine, dicyclohexyl amine, N,N'-diisopropylethylene diamine and N-methyl-cyclohexyl amine.

The first reports of amine salts of rosuvastatin are of a more recent date. For example, WO 2010/081861 describes the preparation of amine salts of rosuvastatin and their use in the preparation of the calcium salt of rosuvastatin. Amines disclosed by WO 2010/081861 include sec-butyl amine, tert-butyl amine, cycloheptyl amine and cyclopentyl amine. Other amine salts of rosuvastatin are disclosed in WO 2012/073256 (rosuvastatin salts of lysine, arginine, triethanol amine, ethanol amine, choline, epolamine, meglumine and ethylene diamine), WO 2012/063115 (rosuvastatin salts of thioureas, heterocyclic amines such as tetrahydrofurfuryl amine, azoles, amino acids, triazoles and pyridines); WO 2012/046193 (rosuvastatin salts of histidine and lysine); WO 2010/035284 (rosuvastatin salts of (S)-2-amino-3,3-dimethyl butane and (S)-(−)-α-methylbenzyl amine), WO 2001/60804 (rosuvastatin salts of ammonium, methyl ammonium, ethyl ammonium, diethanol ammonium, tri(hydroxymethyl)-methyl ammonium, benzyl ammonium, and 4-methoxybenzyl ammonium) and WO 2005/077916 (rosuvastatin salts of cyclohexyl ammonium, diisopropyl ammonium, isopropyl ammonium, dicyclohexyl ammonium, and (S)-(+)-α-methylbenzyl ammonium).

For pitavastatin, the number of disclosures of amine salts is more limited. In EP 742209 short chain (1-3) alkyl amine salts of pitavastatin are disclosed, in WO 2007/132482 the arginine salt is disclosed while WO 2012/106584 discloses diethanol amine and meglumine salts of pitavastatin.

Driven by the pressure to avail medication such as HMG-CoA reductase inhibitors at affordable prices, industry is in constant need for process rationalization and optimization. There is thus a need for starting substances and intermediates that are of high purity that can be prepared using simple and low cost techniques. From this perspective, it is an aim of the invention to provide alternative amine salts of HMG-CoA reductase inhibitors that can be used in the production of HMG-CoA reductase inhibitors.

DETAILED DESCRIPTION OF THE INVENTION

In a first aspect the invention provides an amine salt of HMG-CoA reductase inhibitors wherein said amine is unsaturated. It was surprisingly found that HMG-CoA reductase inhibitors readily form salts with unsaturated amines and crystallize once they are formed. It has been found that crystals of the unsaturated amine salt of the desired HMG-CoA reductase inhibitor of high purity may be obtained from solutions comprising a large number of impurities and undesired HMG-CoA reductase inhibitor analogs.

In a first embodiment the amine is unsaturated. In this respect, the term unsaturated refers to at least one double bond or at least one triple bond between two carbon atoms. The unsaturated amine may be straight, branched or cyclic. Preferred examples are allyl amine, 3-amino-3-methyl-1-propyne), cumyl amine, 2-furfuryl amine, 3-furfuryl amine and propargyl amine (3-amino-1-propyne).

In a second embodiment the unsaturated amine comprises an oxygen atom and preferably said oxygen atom is in the form of an ether bond. The unsaturated amine comprising an oxygen atom may be straight, branched or cyclic. Preferred examples are 2-furfuryl amine and 3-furfuryl amine. Furfurylamine is present as a key structural element in Furosemide (a diuretic used for hypertension and edema), and it is used in skin care cosmetics for anti-aging.

Furfural and derivatives have favorable toxicological properties, see for example "Furfural and Derivatives", H. E. Hoydonkx et al., pp. 285-313, in: Ullmann's Encyclopedia of Industrial Chemistry, 2012, Wiley-VHC Verlag, Weinheim, Germany.

In a third embodiment the HMG-CoA reductase inhibitor preferably is atorvastatin, fluvastatin, pitavastatin or rosuvastatin. It has been found that formation of the amine salt of a HMG-CoA reductase inhibitor can be combined in a single process step with the deprotection sequence that is usually required in the synthesis of HMG-CoA reductase inhibitors that are made through total synthesis. During production carboxyl and hydroxyl functions of these molecules need to be protected and protective groups are removed at the final stage of the synthesis. Removal of protective groups usually includes an acidic treatment. It was found that the amines of the present invention not only are suitable for formation of stable and pure salts but simultaneously can function to neutralize acidic conditions, thereby preventing the formation of additional foreign salts.

In a second aspect, the present invention provides a process for the preparation of salts of HMG-CoA reductase inhibitors with amines as specified in the first aspect of the invention.

In one embodiment, the process may be performed as follows. A protected derivative of the HMG-CoA reductase inhibitor, for example the methyl ester of pitavastatin acetonide or rosuvastatin acetonide, is dissolved or suspended in a suitable solvent, for example acetonitrile. Removal of protecting groups may be carried out by treatment with acid followed by treatment with base, or vice versa. Optionally the organic solvent may be changed by distillation followed by addition of a second solvent, for example ethyl acetate. Preferably the aqueous phase is removed after which the amine of choice is added to the organic phase. Preferably the amount of amine added is from 1.0 to 2.0 mole-equivalents compared to the HMG-CoA reductase inhibitor. The resulting mixture can optionally be concentrated in order to reduce mother liquor losses, if any. The desired amine salt of the HMG-CoA reductase inhibitor precipitates or crystallizes and can be isolated following simple techniques known to the skilled artisan, such as centrifugation, decantation, filtration and the like. Preferably the salt thus obtained is washed with the same solvent as used for the crystallization/precipitation process. Optionally the amine salt of the HMG-CoA reductase inhibitor may be re-crystallized, for instance from an alternate solvent such as acetonitrile.

It was found that furfurylamine, having a boiling point of 145° C., can be advantageously removed via distillation instead of extraction. In general, not many high-boiling amines can be removed in this way, as they require more lengthy and less economical extraction procedures.

In a third aspect, the present invention provides a process for the preparation of metal salts of HMG-CoA reductase inhibitors. Preferably said metal salts are pharmaceutically acceptable, examples of which are calcium and magnesium. Contrary to the teaching of U.S. Pat. No. 5,403,860 that lower yields are obtained when using the salts of HMG-CoA reductase inhibitors as starting or intermediate substances, we have found that, when using the amine salts of HMG-CoA reductase inhibitors according to the present invention, the yields and the purity of the prepared HMG-CoA reductase inhibitors are equal to or greater than when using the HMG-CoA reductase inhibitors in the lactone form. Thus, it was found that in processes for the synthetic construction of HMG-CoA reductase inhibitors the formation of amine salts of HMG-CoA reductase inhibitors in the synthetic medium, in comparison with the mere metal salts as described in publicly accessible literature, represents an efficient means for the isolation and/or purification of HMG-CoA reductase inhibitors by simple crystallization. The amines which are described in the present invention and which readily form salts with HMG-CoA reductase inhibitors are thus particularly suitable as auxiliary materials or processing aids for the isolation and/or purification of HMG-CoA reductase inhibitors. Accordingly, the novel amine salts of HMG-CoA reductase inhibitors of the present invention are also highly valuable as such.

EXAMPLES

Example 1

Preparation of Amine Salts of Pitavastatin and Rosuvastatin

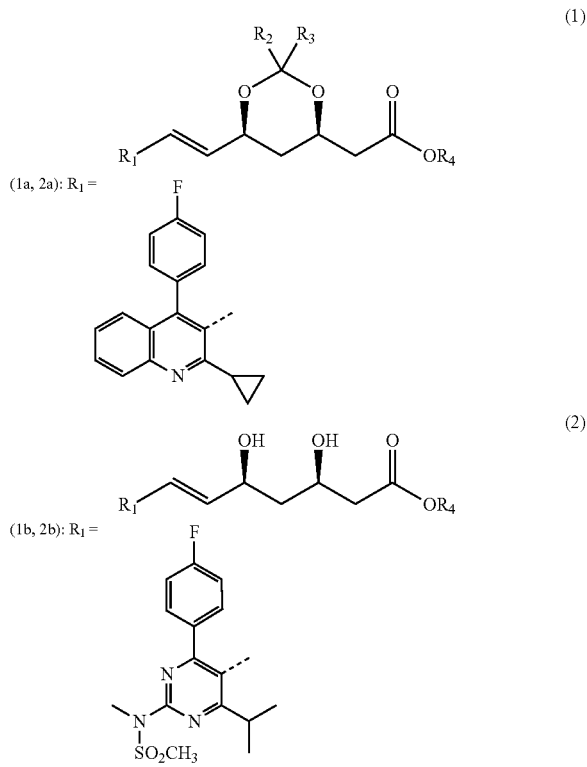

The methyl ester of pitavastatin acetonide (1a, $R_2=R_3=R_4=CH_3$; 5.6 mmol) or rosuvastatin acetonide (1b, $R_2=R_3=R_4=CH_3$; 5.6 mmol) was added to acetonitrile (21 mL). The mixture was heated to 35° C. until complete dissolution was obtained. To the solution 0.02 N aqueous HCl (9 mL) was added over a period of 1 h. The mixture was stirred for 12 h, followed by addition of 1 N aqueous NaOH in 15 min until pH=12. After stirring for 1 h, the mixture was concentrated under vacuum to remove acetonitrile. Next, ethyl acetate (30 mL) was added followed by addition of 1 N aqueous HCl until pH=4. The ethyl acetate phase was separated. To the ethyl acetate phase was added over a period of 30 min, 1 equiv. (5.6 mmol) of amine (see Table below) dissolved in ethyl acetate (10 mL). Upon addition, a white precipitate was formed. The resulting slurry was stirred for 1h, followed by filtration of the amine salt of the HMG-CoA reductase inhibitor pitavastatin or rosuvastatin. The amine salt was washed with ethyl acetate (2×5 mL), dried and re-crystallized from acetonitrile.

| HMG-CoA Reductase Inhibitor | Amine | Product Formula | $R_4$ |
|---|---|---|---|
| Pitavastatin | 2-Furfuryl amine | 2a | furfuryl-CH$_2$-NH$_3^+$ |
| Pitavastatin | Propargyl amine | 2a | HC≡C-CH$_2$-NH$_3^+$ |
| Rosuvastatin | 2-Furfuryl amine | 2b | furfuryl-CH$_2$-NH$_3^+$ |
| Rosuvastatin | Propargyl amine | 2b | HC≡C-CH$_2$-NH$_3^+$ |

Example 2

Preparation of the Calcium Salts of Pitavastatin and Rosuvastatin

The amine salt of the HMG-CoA reductase inhibitor pitavastatin or rosuvastatin obtained in Example 1 was added to water (20 mL) and the pH was adjusted to 12 with 1 N aqueous NaOH. The reaction mixture was extracted with ethyl acetate (20 mL). The organic phase was separated and the aqueous phase was concentrated to 15 mL. To the obtained clear aqueous solution was added in portions over a period of 1 h, 7 mL of a solution of 4.5 w/w % Ca(OAc)$_2$.H$_2$O in water. Upon addition white precipitate was formed. After 1 h the precipitate was filtered and dried to give the calcium salt of pitavastatin or rosuvastatin as a white solid.

Example 3

Preparation of rosuvastatin-Ca ((2b), $R_4=Ca^{2+}$) from ((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate methyl ester ((1b), $R_2=R_3=R_4=CH_3$)

2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate methyl ester (3.0 g, 5.6 mmol) was added to acetonitrile (21 mL). The mixture was heated to 35° C. until complete dissolution was obtained. To the solution, 0.02 N aqueous HCl (9 mL) was added over a period of 1 h. The mixture was stirred for 12 h, followed by addition of 1 N aqueous NaOH in 15 min until pH=12. After stirring for 1 h, the mixture was concentrated under vacuum to remove the acetonitrile. Next ethyl acetate (30 mL) was added followed by addition of 1 N aqueous HCl until pH=4. The ethyl acetate phase was separated. To the ethyl acetate phase was added over a period of 30 min, 1 equiv. of the amine dissolved in ethyl acetate (10 mL). Upon addition, a white precipitate was formed. The resulting slurry was stirred for 1 h, followed by filtration of the rosuvastatin-amine salt. The salt was washed with ethyl acetate (2×5 mL) and dried. The salt was re-crystallized from acetonitrile.

The salt was added to water (20 mL) and the pH was adjusted to 12 with 1 N aqueous NaOH. The reaction mixture was extracted with ethyl acetate (20 mL) and the organic phase was separated. The aqueous phase was concentrated to 15 mL. To the obtained clear aqueous solution was added in portions over a period of 1 h, 7 mL of a solution of 4.5 w/w % Ca(OAc)$_2$.H$_2$O in water. Upon addition white precipitate was formed. After 1 h the precipitate was filtered and dried to give 2.1 g of the calcium salt of rosuvastatin as a white solid (yield 72%). $^1$H NMR (300 MHz, DMSO): δ7.72 (dd, 2H), 7.29 (t, 2H), 6.51 (d, 1H), 5.54 (dd, 1H), 4.21 (dd, 1H), 3.71 (m, 1H), 3.55 (s, 3H), 3.51-3.41 (m, 4H), 2.09 (dd, 1H), 1.92 (dd, 1H), 1.57-1.42 (m, 1H), 1.36-1.25 (m, 1H), 1.22 (dd, 6H).

Example 4

Preparation of rosuvastatin-Ca ((2b), $R_4=Ca^{2+}$) from 2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate methyl ester ((1b), $R_2=R_3=R_4=CH_3$) via furfuryl amine salt

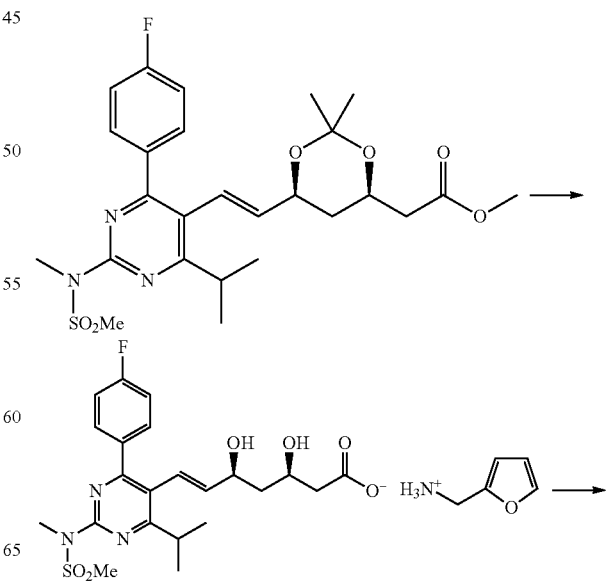

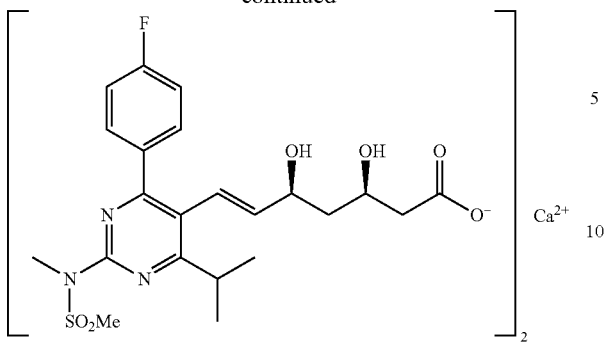

2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate methyl ester (3.0 g, 5.6 mmol) was added to acetonitrile (21 mL). The mixture was heated to 35° C. until complete dissolution was obtained. To the solution, 0.02 N aqueous HCl (9 mL) was added over a period of 1 h. The mixture was stirred for 12 h, followed by addition of 1 N aqueous NaOH in 15 min until pH=12. After stirring for 1 h, the mixture was concentrated under vacuum to remove the acetonitrile. Next ethyl acetate (30 mL) was added followed by addition of 1 N aqueous HCl until pH=4. The ethyl acetate phase was separated. The ethyl acetate phase was heated to 50° C. Then furfurylamine (0.82 g, 8.4 mmol, 1.5 equiv.) dissolved in ethyl acetate (10 mL) was added in 10 min. Upon addition, a white precipitate was formed. The reaction mixture was cooled to 20-25° C. and stirred for 2 h, followed by filtration of the rosuvastatin furfuryl amine salt. The salt was washed with ethyl acetate (2×5 mL) and dried. The salt was added to acetonitrile (20 mL) and heated to 60° C. until complete dissolution. The solution was cooled to 20-25° C. and the resulting slurry was stirred for 2 h. The rosuvastatin furfuryl amine salt was isolated by filtration, washed with acetonitrile (2×5 mL) and dried.

The salt was added to water (20 mL) and the pH adjusted to 3 with 1N aqueous HCl. The reaction mixture was extracted with MTBE (20 mL). The organic phase was separated and extracted with 1N aqueous NaOH. The aqueous phase was separated and concentrated to 15 mL. To the obtained clear aqueous solution was added in portions over a period of 1 h, 7 mL of a solution of 4.5 w/w % Ca(OAc)$_2$·H$_2$O in water. Upon addition white precipitate was formed. After 1 h the precipitate was filtered and dried to give the calcium salt of rosuvastatin as a white solid (2.1 g, yield 72%). From the filtrate, the Rosuvastatin can be recovered in order to increase the overall yield. For example, this can be done, after acidification to pH=4 and extraction with methyl tert butylether by formation of the amine salt as described in this example. In another embodiment, this filtrate can be combined with the extraction procedure as described in the example leading to a single step.

Example 5

Preparation of rosuvastatin-Ca ((2b), $R_4$=Ca$^{2+}$) from 2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate methyl ester ((1b), $R_2$=$R_3$=$R_4$=CH$_3$) via propargyl amine salt

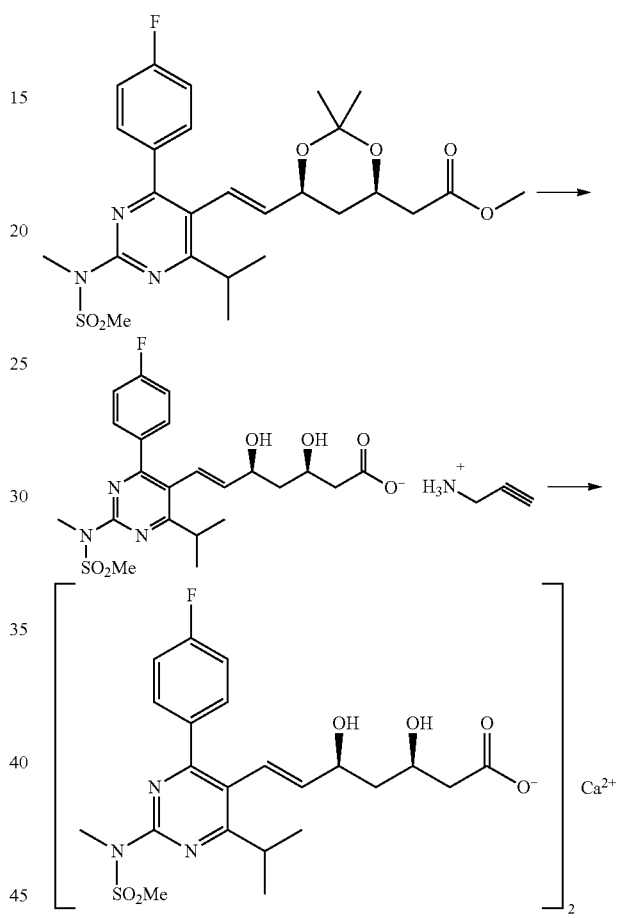

2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate methyl ester (3.0 g, 5.6 mmol) was added to acetonitrile (21 mL). The mixture was heated to 35° C. until complete dissolution was obtained. To the solution, 0.02 N aqueous HCl (9 mL) was added over a period of 1 h. The mixture was stirred for 12 h, followed by addition of 1 N aqueous NaOH in 15 min until pH=12. After stirring for 1 h, the mixture was concentrated under vacuum to remove the acetonitrile. Next ethyl acetate (30 mL) was added followed by addition of 1 N aqueous HCl until pH=4. The ethyl acetate phase was separated. The ethyl acetate phase was heated to 50° C. Then propargyl amine (0.46 g, 8.4 mmol, 1.5 equiv.) dissolved in ethyl acetate (10 mL) was added in 10 min. Upon addition, a white precipitate was formed. The reaction mixture was cooled to 20° C. and stirred for 3 h, followed by filtration of the salt. The salt was washed with ethyl acetate (2×5 mL) and dried. The salt was added to acetonitrile (20 mL of) and heated to 40° C. until complete dissolution. The solution was cooled to 20° C. and the resulting slurry was stirred for 2 h. The rosuvastatin propargyl amine salt was isolated by filtration, washed with acetonitrile (2×5 mL) and dried.

The salt was added to water (25 mL) and the pH adjusted to 12 with 1N aqueous NaOH. The solution was concentrated to 15 mL, followed by addition of 7 mL of a solution of 4.5 w/w % Ca(OAc)$_2$.H$_2$O in water in 1 hour. Upon addition white precipitate was formed. After 2 h the precipitate was filtered and dried to give the calcium salt of rosuvastatin as a white solid (2.2 g, yield 74%).

Example 6

Preparation of 2-((4R,6S)-6-((E)-2-(2-cyclopropyl-4-(4-fluorophenyl)quinolin-3-yl)vinyl)-2,2-dimethyl-1,3-dioxan-4-yl)acetate, methyl ester from 2-cyclopropyl-4-(4-fluorophenyl)quinolin-3-carbaldehyde and 2-((4R,6S)-6-((benzo[d]thiazol-2-ylsulfonyl)methyl)-2,2-dimethyl-1,3-dioxan-4-yl)acetate methyl ester

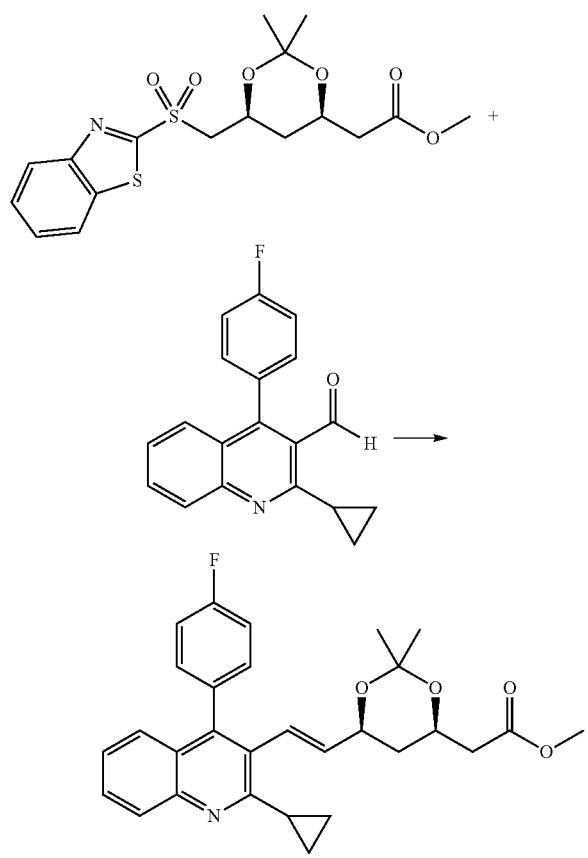

2-((4R,6S)-6-((Benzo[d]thiazol-2-ylsulfonyl)methyl)-2,2-dimethyl-1,3-dioxan-4-yl)acetate methyl ester (35.0 g, 87 mmol) and 2-cyclopropyl-4-(4-fluorophenyl)quinolin-3-carbaldehyde (23.9 g, 82 mmol) were added to 78 mL of N-methyl-2-pyrrolidone and 280 mL of 2-methyltetrahydrofuran. The mixture was heated until 50° C. and filtered. The solution was cooled to −62° C., followed by addition of 54 mL of 2M NaO—tBu in tetrahydrofuran (108 mmol) in 2.5 h keeping the temperature between −55 and −60° C. The temperature was allowed to increase to −20° C. and quenched with 200 mL of water. The mixture was transferred to another reactor using 30 mL of 2-methyltetrahydrofuran and the reaction mixture heated to 50° C. The pH was adjusted to 12 with 29 mL of 4N aqueous NaOH. The layers were separated. The organic phase was washed 2 times with 200 mL of a 5 w/w % aqueous NaCl solution, whereby the pH was adjusted to 12 using 4N aqueous NaOH, followed by 1 time with 100 mL of a 5 w/w % aqueous NaCl solution, whereby the pH was adjusted to 12 with 4N aqueous NaOH. Finally, the organic phase was washed with 100 mL of 5 w/w % aqueous NaHCO$_3$. The organic layer was evaporated to give a thick oil. The solid was re-crystallized from 200 mL of isopropanol to give 2-((4R,6S)-6-((E)-2-(2-cyclopropyl-4-(4-fluorophenyl)quinolin-3-yl)vinyl)-2,2-dimethyl-1,3-dioxan-4-yl)acetate, methyl ester as a white solid (32.1 g, yield 77.6%) with an HPLC purity of 99.7%.

The $^1$H NMR data of this compound were in agreement with the literature data, see Hiyama T.; Minami T.; Yanagawa Y.; Ohara Y. WO 95/11898, 1995 to Nissan Chemical Industries, example 4 of this patent).

Example 7

Preparation of 2-((4R,6S)-6-((E)-2-(2-cyclopropyl-4-(4-fluorophenyl)quinolin-3-yl)vinyl)-2,2-dimethyl-1,3-dioxan-4-yl)acetate, methyl ester from 2-cyclopropyl-4-(4-fluorophenyl)quinolin-3-carbaldehyde and 2-((4R,6S)-6-((benzo[d]thiazol-2-ylsulfonyl)methyl)-2,2-dimethyl-1,3-dioxan-4-yl)acetate methyl ester

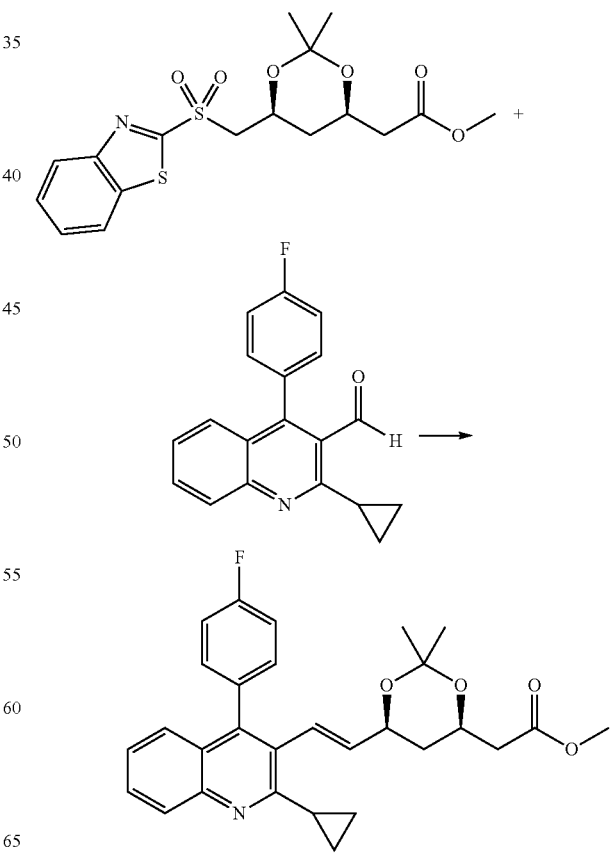

2-((4R,6S)-6-((Benzo[d]thiazol-2-ylsulfonyl)methyl)-2,2-dimethyl-1,3-dioxan-4-yl)acetate methyl ester (30.0 g, 75 mmol) and 2-cyclopropyl-4-(4-fluorophenyl)quinolin-3-carbaldehyde (20.3 g, 70 mmol) were added to 35 mL of N-methyl-2-pyrrolidone and 200 mL of 2-methyltetrahydrofuran at 22° C. The reaction mixture was cooled to −60° C. Then 42 mL of 2M NaO—tBu in tetrahydrofuran (84 mmol) was added in 2.5 h keeping the temperature between −55 and −60° C. The temperature was allowed to increase to −50° C. and quenched with 100 mL of water. The mixture was transferred to another reactor using 30 mL of 2-methyltetrahydrofuran, heated to 50° C. and the pH adjusted to 12.6 with 31 mL of 4N aqueous NaOH. The layers were separated. The organic phase was washed 2 times with 100 mL of a 5 w/w % aqueous NaCl solution, whereby the pH was adjusted each time to 12 using 4N aqueous NaOH. Next, the organic phase was washed with 100 mL of 5 w/w % aqueous NaHCO₃. The organic layer was evaporated to give a thick oil. The solid was re-crystallized from 200 mL of isopropanol to give 2-((4R,6S)-6-((E)-2-(2-cyclopropyl-4-(4-fluorophenyl)quinolin-3-yl)vinyl)-2,2-dimethyl-1,3-dioxan-4-yl)acetate, methyl ester as a white solid (29.0 g, yield 81.3%) with an HPLC purity of 99.5%.

Example 8

Preparation of Pitavastatin-Ca ((2a), $R_4=Ca^{2+}$) from 2-((4R,6S)-6-((E)-2-(2-cyclopropyl-4-(4-fluorophenyl)quinolin-3-yl)vinyl)-2,2-dimethyl-1,3-dioxan-4-yl)acetate methyl ester ((1a), $R_2=R_3=R_4=CH_3$)

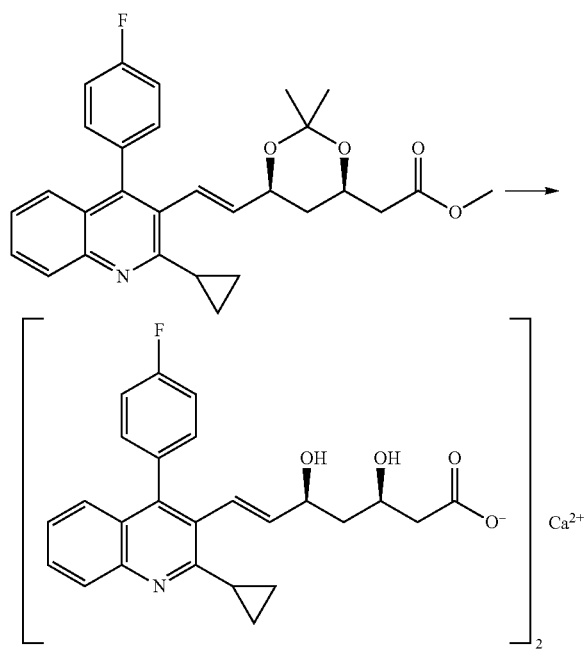

2-((4R,6S)-6-((E)-2-(2-cyclopropyl-4-(4-fluorophenyl)quinolin-3-yl)vinyl)-2,2-dimethyl-1,3-dioxan-4-yl)acetate methyl ester (10.0 g, 21.0 mmol) was added to acetonitrile (50 mL). The mixture was heated to 45° C., followed by addition of 4N aqueous HCl (5.3 mL, 21 mmol). The reaction mixture was stirred for 1.5 h and cooled to 22° C. Then in total 12 mL of 4N aqueous NaOH was added until pH 12.7. After stirring for 30 minutes, the pH was reduced to 9 by addition of acetic acid. The acetonitrile was removed via distillation under vacuum, followed by addition of 30 mL of water. To the clear solution was added over a period of 30 min, 47.3 mL of a solution of 4.5 w/w % Ca(OAc)₂.H₂O in water. Upon addition white precipitate was formed. After 1 h the precipitate was filtered, washed with water (2×15 mL) and dried to give 9.0 g of the calcium salt of Pitavastatin as a solid. HPLC purity 98.8%, KF 2.1% water.

Example 9

Preparation of Pitavastatin-Ca ((2a), $R_4=Ca^{2+}$) from 2-((4R,6S)-6-((E)-2-(2-cyclopropyl-4-(4-fluorophenyl)quinolin-3-yl)vinyl)-2,2-dimethyl-1,3-dioxan-4-yl)acetate methyl ester ((1a), $R_2=R_3=R_4=CH_3$) via furfuryl amine salt

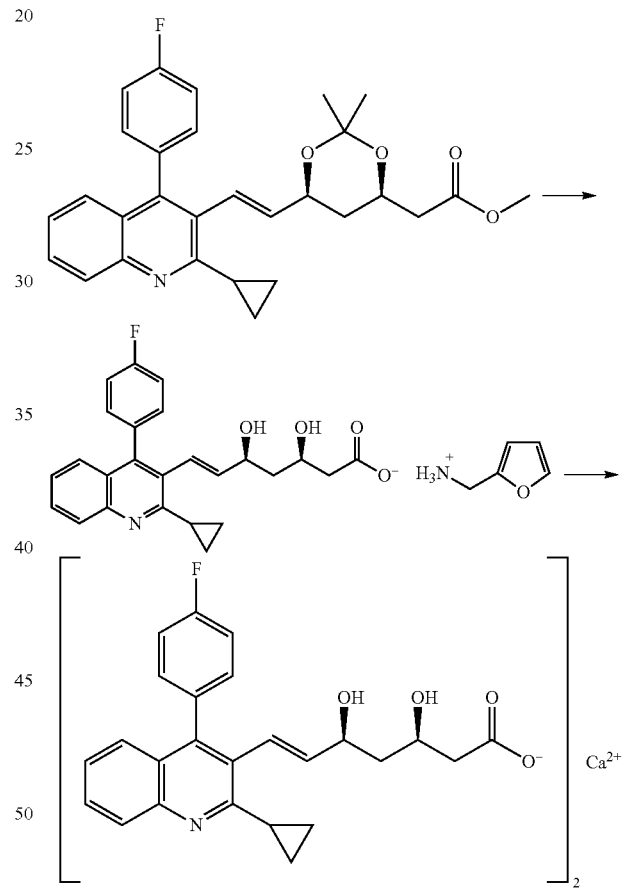

2-((4R,6S)-6-((E)-2-(2-cyclopropyl-4-(4-fluorophenyl)quinolin-3-yl)vinyl)-2,2-dimethyl-1,3-dioxan-4-yl)acetate methyl ester (10.0 g, 21.0 mmol) was added to acetonitrile (50 mL). The mixture was heated to 45° C. and 4N aqueous HCl (5 mL, 20 mmol) was added. The reaction was stirred for 2.5 h. After cooling to 22° C., 4M aqueous NaOH is added over a period of 1.5 h. The pH is reduced to 6.5 by addition of 1N aqueous HCl, and then concentrated under vacuum to remove the acetonitrile. Next methyl tert-butylether (20 mL) was added followed by addition of 1 N aqueous HCl until pH=4. The organic layer was separated and concentrated under vacuum. To the residue was added acetonitrile (68 mL) and water (3.9 mL). The reaction mixture was cooled to 10° C.; Then Then furfurylamine (2.04 g, 21.0 mmol) dissolved in acetonitrile (13.5 mL) was added in 1.5 h. Upon addition, a white precipitate was formed. The reaction mixture was stirred for 30 min, followed by filtration of the Pitavastatin-furfuryl amine salt. The salt was washed with ethyl acetate (2×10 mL) and dried to give 8.3 g of a white solid.

The salt was added to water (100 mL) and the pH adjusted to 12.3 using 3.4 mL aqueous 4N NaOH. The reaction mixture is heated and 3×40 mL of water was removed via distillation under vacuum. After each distillation, the volume distilled water was replaced by adding the same volume of fresh water. After cooling to 22° C., 1 g of active carbon was added. The mixture was stirred for 1 h and the carbon removed by filtration. The pH of the solution was lowered by addition of acetic acid to 9.7 and 20 mL of water was added. Then over a period of 45 min, 33 mL of a solution of 4.5 w/w % $Ca(OAc)_2 \cdot H_2O$ in water was added. Upon addition white precipitate was formed. After 30 minutes stirring, the solid was filtered and dried to give the calcium salt of Pitavastatin as a white solid (7.5 g, KF 2.8%). From the filtrate, the Pitavastatin can be recovered in order to increase the overall yield. For example, this can be done, after acidification to pH=4 and extraction with methyl tert butyl-lether by formation of the amine salt as described in this example. In another embodiment, this filtrate can be combined with the extraction procedure as described in the example leading to a single step.

Comparative Example

Preparation of rosuvastatin-Ca ((2b), $R_4=Ca^{2+}$) from 2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate methyl ester ((1b), $R_2=R_3=R_4=CH_3$) via tert-butyl amine salt

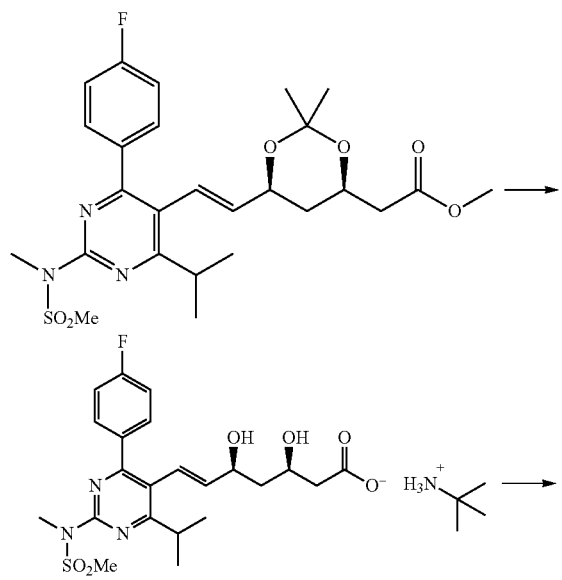

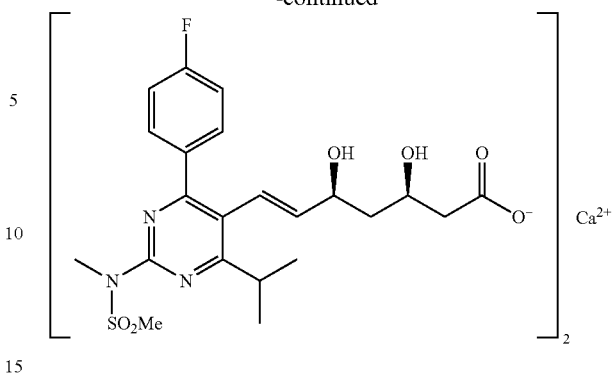

2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate methyl ester (3.9 g, 7.2 mmol) was added to acetonitrile (23 mL). To the mixture was added 0.02 N aqueous HCl (7.7 mL) and stirred for 18 h at 20° C. Then 1N aqueous NaOH was added in 15 min until pH=12. After stirring for 1 h, the mixture was concentrated under vacuum to remove the acetonitrile. Next ethyl acetate (30 mL) was added followed by addition of 1N aqueous HCl until pH=4. The ethyl acetate phase was separated. The ethyl acetate phase was heated to 60° C. and tert-butyl amine (0.8 g, 11.0 mmol, 1.5 equiv.) dissolved in ethyl acetate (10 mL) was added. The reaction mixture was cooled to 40° C., when precipitation occurred. The slurry was further cooled to 20° C. and stirred for 2 h at this temperature. The solid was isolated by filtration and washed with ethyl acetate (2×3 mL) and dried. The salt was added to acetonitrile (19 mL) and water (1 mL) and heated to reflux. The reaction mixture was cooled to 20° C. and stirred for 1.5 h. The rosuvastatin tert-butyl amine salt was isolated by filtration, washed with acetonitrile (2×5 mL) and dried.

The salt was added to water (30 mL) and the pH was adjusted to 12 with 1N aqueous NaOH. The solution was concentrated to 20 mL. The pH was adjusted to 8.5-9 with acetic acid. Then 8 mL of a solution of 4.5 w/w % $Ca(OAc)_2 \cdot H_wO$ in water was added in 1 h. The reaction mixture was stirred for 3 h and the solid isolated by filtration and washed with water (2×5 mL). The solid was dried to give the calcium salt of rosuvastatin as a white solid (2.9 g, yield 80%).

The invention claimed is:

1. An amine salt of pitavastatin or rosuvastatin, wherein the amine is selected from the group consisting of 2-furfuryl amine, 3-furfuryl amine and propargyl amine.

2. The amine salt of claim 1, which is the 2-furfuryl amine salt of rosuvastatin.

* * * * *